United States Patent
Guerrieri

(10) Patent No.: US 9,597,225 B1
(45) Date of Patent: Mar. 21, 2017

(54) NON-INVASIVE THERMAL WRAP METHOD FOR INDUCING CALORIE BURNING AND WEIGHT LOSS

(71) Applicant: Massimo Guerrieri, Great Neck, NY (US)

(72) Inventor: Massimo Guerrieri, Great Neck, NY (US)

(*) Notice: Subject to any disclaimer, the term of this patent is extended or adjusted under 35 U.S.C. 154(b) by 913 days.

(21) Appl. No.: 13/920,373

(22) Filed: Jun. 18, 2013

(51) Int. Cl.
  *A61F 7/00* (2006.01)
  *G09B 19/00* (2006.01)

(52) U.S. Cl.
  CPC .......... *A61F 7/007* (2013.01); *G09B 19/0092* (2013.01)

(58) Field of Classification Search
  CPC combination set(s) only.
  See application file for complete search history.

(56) References Cited

U.S. PATENT DOCUMENTS

| | | | |
|---|---|---|---|
| 8,143,559 B2* | 3/2012 | Chow | A61F 7/02 219/212 |
| 2004/0149711 A1* | 8/2004 | Wyatt | A61F 7/00 219/217 |
| 2009/0312823 A1* | 12/2009 | Patience | A61F 7/007 607/104 |

* cited by examiner

*Primary Examiner* — Joseph Stoklosa
*Assistant Examiner* — Adam Avigan

(57) ABSTRACT

A method for reducing cellulite, local or generalized fat comprising applying thermal body wraps, which are cycled in temperature, is provided. Based on a body composition test, suggested targets for body fat percentage, total weight, fat weight, lean weight, weight to lose, body water percentage and basal metabolic rate are calculated. The thermal body wraps are described and may comprise layers of synthetic material, such as polyurethane and polyester fabric. The body wraps may have a heating circuit including a coaxially arranged heating cable, and a control loop including a negative temperature coefficient thermistor. The heating cable may have a protection wire, coaxially surrounding and insulated from a heating wire, so that if a break in the heating wire is detected, current flow to the heating wire is suspended. A thermostat in the wrap provides additional safety.

11 Claims, 9 Drawing Sheets

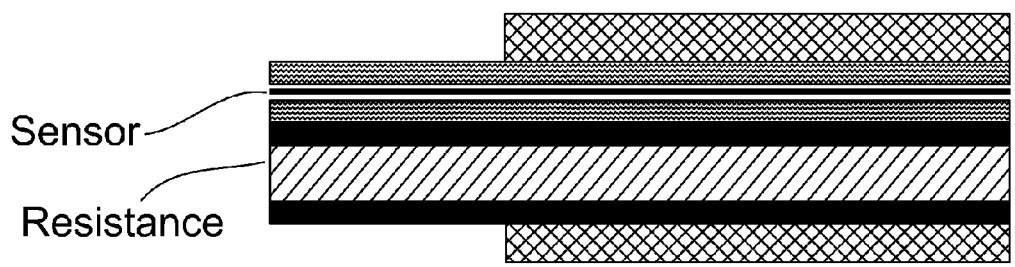
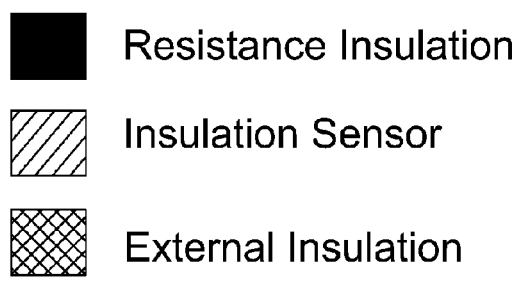
FIG. 4

FIG. 7

PLAN ONE – Big Breakfast - Light Lunch - Dinner

Calories Range [1300-2000]

Big Breakfast
- [60-80] 8:00 am - Snack - 1 Cup Water, 2 Kiwis, or 1 Cup Citrus Fruit Juice
- [70-80] 8:30 am - Breakfast - 1/2 Cup Coffee/Tea, 1/2 Cup Soymilk - PLUS - Three Choices - Choose One:
- [200-350] - 1st Choice - Whole-Wheat Grain Course
  2 Slices Whole-Wheat Toasted Bread or 1/2 Whole-Wheat Bagel with:
  1/2 Tbsp. Honey, or Almond-Butter, or Jam, or Cheese;
  or 1 1/3 Cup Whole-Grain Cereal - OR -
- [95-130] - 2nd Choice - 1 Plain Yogurt and/or 1 Kiwi - OR -
- [360] - 3rd Choice - Animal Protein/Dairy Course
  2 All Natural Eggs, 1 Slice Whole-Wheat Toasted Bread

Light Lunch
- [200] 1:00pm - Light Lunch - 1 Cup Water, 1 Bowl - 2 Servings Dressed Salad - PLUS -
  1 Serving Option:
- [140-240] - 1/2 Cup Chickpeas, or Lentils, or other Beans, or 1/2 Cup Tofu, or 1/2 Avocado, or 1/2 Cup Vegetables, or 1/3 Cup Nuts, or 2 oz. Cheese: Ricotta, or Mozzarella, or Cheddar, or 2-3 oz. Fish, or Poultry, or Meat,
- [80] 5:00 pm - Snack - 1 Cup Water, 1 Whole Peeled Fruit

Dinner
- [200-280] 7:00-7:30pm - Dinner - 1 Bowl - 2 Servings Dressed Salad and/or
  1 Cup Vegetable Soup - PLUS -
  Two Choices - Choose One:
- [525-580] - 1st Choice - Vegetable Protein Course
  1 Cup Chickpeas, or Lentils, or other Beans + 3/4 Cup Vegetables
  - Dressing: 2 tbsp. Extra-Virgin Olive Oil - OR -
- [765-1190] - 2nd Choice - Animal Protein/Dairy Course
  5 oz Fish, or Poultry, or Meat, or 4 oz. Cheese: Ricotta, or Mozzarella, or Cheddar, or 2 All Natural Eggs + 3/4 Cup Vegetables
  - Dressing: 2 tbsp. Extra-Virgin Olive Oil
- [10-80] 11:00 pm - Snack - 1 Cup Green Tea and/or 1 Whole Peeled Fruit

PLAN TWO – Light Breakfast - Lunch - Dinner

Calories Range [1300-2000]

- [60-80] 8:00 am - Snack - 1 Cup Water, 2 Kiwis, or 1 Cup Citrus Fruit Juice
- [10-80] 8:30 am - Light Breakfast - 1/2 Cup Coffee/Tea, and/or 1/2 Cup Soymilk
- [80-130] 10:30 am - Snack - 2/2 Cup Water, 1 Whole Peeled Fruit, or 1 Plain Yogurt

Lunch
- [200] 1:00pm - Lunch - 1 Cup Water, 1 Bowl - 2 Servings Dressed Salad - PLUS -
  Three Choices - Choose One:
- [435-490] - 1st Choice - Vegetable Protein Course
  1 Cup Chickpeas, or Lentils, or other Beans, or 1/2 Avocado, or 1/2 Cup Nuts, or Tofu + 3/4 Cup Vegetables
  - Dressing: 1 Tbsp. Extra-Virgin Olive Oil - OR -
- [785-840] - 2nd Choice - Whole-Wheat Grain Course
  1 Cup Whole-Wheat Pasta, or Brown Rice, or 3 Slices Whole-Wheat Toasted Bread, or 2 Medium Potatoes + 3/4 Cup Vegetables
  - Dressing: 1 Tbsp. Extra-Virgin Olive Oil - OR -
- [510-520] - 3rd Choice - Animal Dairy Course
  4 oz. Cheese: Ricotta, or Mozzarella, or Cheddar, or 2 All Natural Eggs + 3/4 Cup Vegetables - Dressing: 1 Tbsp. Extra-Virgin Olive Oil

Dinner
- [200-280] 7:00-7:30pm - Dinner - 1 Bowl - 2 Servings Dressed Salad and/or
  1 Cup Vegetable Soup - PLUS -
  Two Choices - Choose One:
- [525-580] - 1st Choice - Vegetable Protein Course
  1 Cup Chickpeas, or Lentils, or other Beans + 3/4 Cup Vegetables
  - Dressing: 2 Tbsp. Extra-Virgin Olive Oil - OR -
- [765-1190] - 2nd Choice - Animal Protein/Dairy Course
  5 oz Fish, or Poultry, or Meat, or 4 oz. Cheese: Ricotta, or Mozzarella, or Cheddar, or 2 All Natural Eggs + 3/4 Cup Vegetables
  - Dressing: 2 tbsp. Extra-Virgin Olive Oil
- [10-80] 11:00 pm - Snack - 1 Cup Green Tea and/or 1 Whole Peeled Fruit

[Daily Range Intake of Calories = 1300-2000 / Fiber = 25-30 gr]

NON-INVASIVE THERMAL WRAP METHOD FOR INDUCING CALORIE BURNING AND WEIGHT LOSS

FIELD OF THE INVENTION

The present invention relates to a non-invasive technique designed to help an individual lose weight by burning calories from fatty deposits in the body without strenuous exercise. More particularly, the invention relates to a non-invasive thermal-wrap therapy for inducing calorie burning and weight loss. The thermal-wrap therapy helps burn over 5,000 calories per week without strenuous exercise, is effective without radical dieting, pills or medication, is non-invasive and safe, and achieves the desired results after just one week of treatment with bi-weekly sessions.

BACKGROUND OF THE INVENTION

Cellulite has been defined as "deposits of subcutaneous fat within fibrous connective tissue (as in the thighs, hips and buttocks) that give a puckered and dimpled appearance to the skin surface." The origin of the term is French, where it literally means accumulation of subcutaneous fat, cellulitis, from cellule (cell) and ite (itis). The medical definition of cellulite is "deposits of subcutaneous fat within fibrous connective tissue (as in the thighs, hips and buttocks) that give a puckered and dimpled appearance to the skin surface." Cellulite is known as localized lipodystrophy, meaning misshapen fat in one or several specific areas of the body.

"Cellulite" is not a medical term. In the past, cellulite has been widely interpreted as a fat disorder. However, medical research has discovered that it is, in fact, primarily a disease of the circulatory system that deforms the connective tissue. Though infrequently found in males, it is found in some 95% of women today. It is seen more commonly in males with androgen-deficient states such as Klinefelter's syndrome, hypogonadism, post-castration states and in those patients receiving estrogen therapy for prostate cancer.

Medical authorities agree that cellulite is simply ordinary fatty tissue. In testing, cellulite has been found to be indistinguishable from ordinary fat. Strands of fibrous tissue connect the skin to deeper tissue layers and also separate compartments that contain fat cells. When fat cells increase in size, these compartments bulge and produce a waffled appearance of the skin.

Cellulite follows a predictable path of development. It typically starts with a few broken veins or tiny areas of discoloration and a tendency to bruise easily. This early stage may be missed, but it soon develops into the distinctive "orange peel" appearance as the tissue under the skin becomes swollen and distended. If left unchecked, this frequently develops into the "mattress skin" stage in which the skin feels cool. After this, the tissues deteriorate further into islands of concentrated blood flow that feel hot and are surrounded by cold cellulite tissue. The lack of circulation in the damaged cellulite tissues finally results in more fat along with fluid retention to produce a honeycomb structure of swollen lumpy tissue, known as steatomes, that disfigures the body profile.

Cellulite is caused by damage to the delicate capillary or drainage system in the fat layer under the skin. It begins when the circulation in the capillaries, veins or lymphatic drainage vessels under the skin slows down. This leads to sluggish or even static regions of blood or lymph flow, which allow highly reactive chemicals, known as free radicals, to attack the walls of the capillaries, veins or lymph vessels as well as the surrounding tissues. Once damage has occurred in one of the circulatory systems in this fatty layer, it spreads to the others, leading to accumulation of lymph in the tissues.

As the circulation slows and lymph accumulates in the fatty tissue under the skin, more and more protein fibers are formed. Normally, cells known as fibroblasts would dissolve these abnormal protein fibers, but as the circulation and drainage deteriorate, these fibroblasts become defective because they are starved of oxygen and nutrients. Instead of removing the protein fibers and maintaining a network of fine, elastic, supporting fibers, they build thicker, less flexible webs of fiber around groups of fat cells. These fibers give rise to a lumpy appearance on the skin that is the beginning of the cellulite cycle.

Fat cells have fat-storing and fat-releasing receptor sites. Different parts of the body have fat cells with more fat storing sites or more fat-releasing sites. This is why many women tend to store fat on certain parts of the body and lose it on other parts, frequently giving rise to the familiar "pear shaped" body or "Gynoid" conformation.

Cellulite areas usually have fat cells with more fat-storing sites. This means that any fatty substances in the lymph surrounding the damaged tissues are quickly taken up by the fat cells and stored. During exercise, the body demands energy from the fat cells to release fat into the blood for consumption by the muscles. The damaged cellulite tissues, however, are not able to respond due to the damaged circulation. As a result, fat from other areas is used and the cellulite areas continue to build up fatty deposits.

Research has identified two types of cellulite. The first type of cellulite is from any "pinch" or "compression" of tissue in the thighs or buttocks. This type of cellulite is gender-typical to almost all women of various ages.

The second type of cellulite is the "mattress" or "orange peel" appearance that a woman may have in her natural stance or when lying down. An example of this type is the "mattress" look in thighs when crossing legs while seated. The combination of thick, rigid fibers and increasing fat along with distended tissues caused by fluid retention gives rise to the "orange peel" appearance of the skin that is associated with the first stages of cellulite. Without appropriate and preventative treatments, the cycle of damages accelerates causing patches of isolated fatty tissue that feel cold, separated by "hot" zones where blood circulation is concentrated. This is known as the "mattress skin" stage, which progresses to the formation of steatomes.

It was thought previously that cellulite was related to obesity, yet it is found on skinny women and men.

A. Genetic

It is well known that women possessing the Mediterranean conformation, or "Gynoid" conformation ("pear shaped" body), or both, have localized cellulite and fat on their hips and thighs.

B. Damaged Circulation

There are many ways that the very delicate microcirculation and lymph drainage vessels under the skin can be damaged. It is certain that free radicals play a role in this damage and it is likely that physical damage or restriction is also involved in starting the cycle of deterioration that results in cellulite. Examples of this physical damage or restriction are: sitting for long periods, wearing tights, over exertion while training, etc.

If either the incoming fresh blood, or the outgoing "used" blood is restricted, free radicals start to build up and oxygen becomes scarce. This causes more damage to the circulation as well as impairing the function of the cells, known as fibroblasts, that manage the structure of the connective tissue.

When fibroblasts malfunction, they cause two problems: (1) they weaken the fibers that hold the fat cells in place; and (2) they coat clumps of fat cells with impenetrable protein layers that prevent the circulation from reaching these areas.

C. Free Radicals

Free radicals are highly reactive chemicals that are found everywhere in the environment and in our bodies. They react with almost everything they come in contact with and are very damaging. Besides cellulite, they are responsible for aging and cause many of the worst diseases we suffer from, including cancer, heart disease, and Alzheimer's disease. Free radicals are the main agents of damage to our circulatory system that results in cellulite.

We are constantly taking in free radicals from the environment as well as creating them within every cell in our body. Free radicals are leftover pieces of molecules which include oxygen but are lacking one or more electrons. Our immune system may use them to destroy unwanted elements such as bacteria, viruses, and cancer cells. Unfortunately, the destruction of these invaders includes considerable collateral damage, as the free radicals are not specific and react with anything that can supply the electrons they need.

Whether we create the free radicals or absorb them from our food or environment, the results are the same: cell walls are weakened and the genetic DNA molecules become damaged. Over time, this may lead to slow circulation, a factor in the production of cellulite, heart attacks, strokes, Alzheimer's, cancer, etc.

Our bodies protect themselves from the continuous onslaught of free radicals with agents known as antioxidants; these include vitamins, enzymes and many herbal extracts. They are abundantly available in fresh herbs, fruit, and vegetables, particularly immediately after they have been harvested and when they have been organically grown. Vitamins C and E, as well as beta-carotene (the building block for vitamin A), have been found to be particularly effective. Even more powerful are certain herbal extracts that act as antioxidants.

D. Over Exertion

Over exertion causes a build-up of free radicals in the tissues. Tissues under the skin are vulnerable to damage, particularly in women, so any accumulation of excess free radicals in this area may cause damage to the microcirculation and vessels. The body can manage free radicals caused during short bursts or over exertion, such as those expended in team or competitive sports and weight or resistance training. If over exertion is sustained, however, as in long distance running and competitive athletics, damage from free radicals may begin to accumulate.

E. Digestion and Bad Diet

When partially chewed food reaches the large intestines, where digestion occurs through the action of friendly bacteria, clumps of unprocessed food attract unfriendly bacteria and provide a rich medium for them to multiply. This results in the production of poorly digested food molecules that not only damage the intestine, but also are absorbed into the body. These toxic residues are delivered to the liver where they are broken down into harmless molecules and removed from the body via the gall bladder or kidneys. Our livers, can, however, only deal with a limited amount of these toxins, and any excess is sent to the fat cells where they are held so as to protect the body from damage. These toxins cause fluid and fat retention in the cells, which then swell up and reduce blood circulation and block the lymph from draining properly. Reduced lymph drainage and poor blood circulation causes fat accumulation, stretching of the connective fibers under the skin and the bulging pattern of the skin characteristic of cellulite.

As the circulation in the skin deteriorates with the early onset of cellulite, these toxic residues become isolated and are implicated in the development of cellulite as the familiar "orange peel" and "mattress skin" takes shape.

F. Hormonal Imbalances

The female hormone Estrogen is responsible for shortening the fibrous tissue that closes the womb just before delivering a baby. An excess of Estrogen or contraceptive pills are believed to cause weakening of the connective tissue which allows fat to bulge up into the skin. Excess Estrogen is thought to be one of the main causes of cellulite.

G. Chemicals and Artificial Products

Drugs, artificial hormones and artificial products can cause cellulite, as the body does not have the capability of naturally eliminating such chemicals. One of the only means of eliminating chemicals from the body is to store them in fat tissue. It is well known that the chemical compound, DDT, used many years ago to destroy mosquitoes and other insects remains to this day deposited in the fat cells of people who were exposed to it.

Efforts have been employed to reduce cellulite. Liposuction is not very successful in treating cellulite and may actually worsen the dimpled skin appearance. Biochemicals such as aminophylline, caffeine and theophyilline, members of a group known as methylxanthines, are present in many cellulite creams. These agents can enhance the body's ability to break down stored fat, a process known as lipolysis. When applied topically to the skin, however, the cellulite cream must be able to penetrate the skin and dermis and reach the target fat tissue before being absorbed by the tissue. Yet, to be effective, these creams would have to have a sufficient concentration in the subcutaneous fat layer for an ample length of time, which partially explains their lack of consequential cellulite removal. While studies have shown a small reduction in thigh girth when using such creams, there has not been a substantial reduction in the presence of cellulite.

It has been claimed that the only effective way to reduce cellulite is the same one which reduces ordinary fat, that is, exercise. The inventor is not aware, however, of any proven method, system or study that has proven the efficacy of strenuous exercise in reducing cellulite, local or generalized fat, but are aware that there is research showing that strenuous exercise can be useless and can, in fact, exacerbate the presence and appearance of cellulite. In addition, strenuous exercise can pose a danger for women after the menopausal stage and men after age 55, particularly causing back, joint and muscle problems. In any event, the available data and/or statistics support the position that more than 75% of the population of the Western hemisphere does not engage in regular exercise.

The method of the invention provides a means of losing weight, reducing inches and the burning of more than 5,000 calories in one week with bi-weekly sessions without strenuous exercise using thermal wrap therapy. This therapy uses a conductive heating system encased in a specifically designed fabric. This system works as a localized "mini sauna" to enhance sweating and detoxification. The thermalwraps can either be applied locally to thighs, hips and abdomen or over the entire body for more generalized results. Its effectiveness is increased by instituting a Mediterranean alkalinizing eating plan that is customized to each individual's needs. The weight loss of this technique consists of over 78% from fatty deposits while increasing the body's water content. What this means is that not only is the percentage of fat that is burned maximized, but the loss of lean muscle and water is minimized. In addition to the significant weight loss, it was also observed that this integrative approach has other benefits including detoxification, relaxation to diminish stress, and anti-aging and alkalinizing benefits.

More particularly, the method and technique of the invention provides a means of losing weight, reducing inches and the burning of more than 5,000 calories in one week with bi-weekly sessions utilizing the invention without strenuous exercise using thermal wrap therapy. The inventor has been able to demonstrate using the disclosed technique that the weight loss observed consists of over 78% from fatty tissue while increasing the body water content.

Adipose tissue, also known as local fat, is primarily located beneath the skin, but is also found around internal organs. The fat layer of skin is located in the subcutaneous layer of tissue called the hypodermis. In the skin, it accumulates in the deepest level, the subcutaneous layer, providing insulation from heat and cold. Around organs, it provides protective padding. It also functions as a reserve of nutrients.

In overweight and obese persons, excess adipose tissue hanging downward from the abdomen is referred to as a panniculus (or pannus). A panniculus complicates surgery of the morbidly obese, and may remain as a literal "apron of skin" if a severely obese person quickly loses large amounts of weight.

There are two types of adipose tissue: white adipose tissue and brown adipose tissue. White adipose tissue, also known as white fat, constitutes as much as 20% of body weight in men and 25% of body weight in women. Brown adipose tissue, also known as brown fat, is present in many newborns.

Generally speaking, when a person introduces the right amount of caloric intake into the daily diet, in other words, eats with moderation and exercises regularly, that person has a greater chance of keeping weight under control. The problem is that, as set forth above, many people do not exercise regularly and tend to eat too much. Moreover, certain foods are lacking in nutrients and water. Other causes of overweight or obesity today are: genetic, metabolic, psychological, socio-cultural, lifestyle, hormone dysfunction, over eating, and high caloric intake. The inventor has been able to demonstrate that, with just two 50-minute thermal wrap sessions in accordance with the invention per week, the subject would burn over five times the calories as jogging on a treadmill, as demonstrated by FIG. 8.

In the clinical setting, overweight and obesity are typically evaluated by measuring BMI (body mass index) and waist circumference. The BMI, developed by the Belgian Adolphe Quetelet, is calculated by dividing the subject's weight in kilograms by the square of his/her height in meters (BMI=kg/m$^2$). The current definitions commonly in use establish the following values:

Group A—a BMI of 18.5-24.9 is normal weight;
Group B—a BMI of 25.0-29.9 is overweight;
Group C—a BMI of 30.0-39.9 is obese; and
Group D—a BMI of 40.0 or higher is severely (or morbidly) obese.

Due to the size restrictions of the body wraps, more fully discussed below, Groups A and B are the preferable subjects for the treatment outlined in the invention.

The eating plan preferably combined with the thermal wrap technology is a versatile, comprehensive program, modeled on the Mediterranean diet, for altering an individual's eating patterns in order to both meet nutrient requirements and help control weight in a healthy, satisfying manner. The plan allows the individual to tailor food choices to personal preferences. Designed to conform to the U.S. Dietary Guidelines, it emphasizes choosing fiber-rich fruits, vegetables, and whole-grain products, but does not exclude nutrient-rich choices from the dairy and protein food groups, thus ensuring a wide variety of nutrient sources.

With just two 50-minute thermal-wrap sessions per week, over five times the amount of calories are burned then would be burned while jogging on a treadmill. Table I set forth above sets forth the comparison in calories burned.

SUMMARY OF THE INVENTION

In accordance with the invention, a method is provided for treating cellulite and reducing the volume of fat cells localized in the subcutaneous areas by the use of heat applied to the affected areas. The application of heat results in a restoration and improvement of the lymphatic and blood circulation to the tissues. The fat deposits lying under the epidermal cells are stimulated by the heat applications. Heat applied to the human body has the effect of drawing fresh blood with nutrients and oxygen closer to the surface of the skin. In so doing, the fat deposits are drawn out of the tissues, thereby neutralizing the build-up of damaging positive ions and creating an environment that allows the blood supply to be rebuilt by the body. The method for reducing cellulite, local or generalized fat in accordance with the invention utilizes variable temperatures and comprises the following steps in the sequence which follows:

(a) applying a heat source, having a temperature, i.e., the heat source (thermal wrap) has been preheated to a temperature within the temperature range of about 104° F. to about 108° F. (first temperature), to the area on the body of a person affected with cellulite or local fat;

(b) increasing the temperature of said heat source over approximately the next twelve to fifteen minutes to a second temperature in the range of about 122° F. to about 128° F., and preferably about 124° F. to about 126° F.;

(c) decreasing the temperature of said heat source over approximately the next one and one-half minutes to a third temperature differing from said second temperature by having a lower value than said second temperature and being in the range of about 112° F. to about 120° F., and preferably about 110° F. to about 114° F.;

(d) increasing the temperature of said heat source over approximately the next three and one-half minutes to a temperature differing from said third temperature by having a value higher than said third temperature and being in the range of about 122° F. to about 128° F., and preferably about 124° F. to about 126° F., and most preferably increasing the temperature to a value substantially equivalent to the second temperature (step (b), above); and (e) repeating a cycle of the steps (c) and (d) nine or ten times until a period of about 45 minutes to about 60 minutes has elapsed from the time that said heat source was applied to said affected area.

Most, preferably, the method for reducing cellulite, local or generalized fat in accordance with the invention comprises the following steps in the sequence which follows:

(f) applying a heat source, having a temperature, i.e., the heat source (thermal wrap) has been preheated to a temperature within the temperature range of about 104° F. to about 114° F., and preferably about 106° F. to about 108° F. (first temperature), to the area on the body of a person affected with cellulite or local fat;

(g) increasing the temperature of said heat source over approximately the next ten to fifteen minutes to a second temperature in the range of about 123° F. to about 127° F.;

(h) decreasing the temperature of said heat source over approximately the next one and one-half minutes to ten minutes to a third temperature differing from said second temperature and being in the range of about 113° F. to about 119° F., and preferably about 110° F. to about 114° F.;

(i) increasing the temperature of said heat source over approximately the next three and one-half minutes to a temperature differing from said third temperature and being in the range of about 123° F. to about 127° F., and preferably about 124° F. to about 126° F.; and (j) repeating a cycle of the steps (c) and (d) nine or ten times until a period of about 50 minutes to about 55 minutes has elapsed from the time that said heat source was applied to said affected area.

The method, in accordance with another preferred embodiment of the invention, may include showering at a certain temperature or range of temperatures for specified time periods following the heat applications. Also, the method may preferably include the adherence to an eating plan.

The actual wrap employed (Thermal-Wrap 5000™, Vivinlinea Corporation, Great Neck, N.Y.) has been shown to be safe with no adverse effects (Lovisolo, G. A., Marino C., c/o ENEA Labs, Casaccia Research Center, report available upon request). Its design uses a conductive heating system with resistive elements causing the heat to gently penetrate deeper into the skin in a safe and controlled manner.

During use, the researchers observed an increase of 7° F. or more on the superficial layer of the skin and up to 10 mm of depth. Core temperatures increased 0.6° F., typical of that observed during sporting activity.

The apparatus of the invention can be characterized as a conductive heating system utilizing variable temperatures and comprises 2 parts: (1) a controller or control board to be operated by a trained individual; and (2) 3 heating structures, called "thermal wraps," that induce modulated and gentle heat in cutaneous and subcutaneous areas. The heating structure may comprise 3 separate wraps or be consolidated into a single body wrap. The maximum extremely low-frequency electric field (ELF) was 11 µT.

Each thermal wrap contains a series of insulated electrical resistances that the controller to provide a 50 to 60 Hz current at 24V and a power of 600 W at maximum.

The conductive heating system and method for reducing cellulite of the invention utilizing variable temperatures also provides for an apparatus for reducing cellulite, local or generalized fat, comprising (a) a heat source and (b) an electrical energy supplying device for regulating an electrical current to produce a first temperature of the heat source of about 104° F. to about 114° F., and preferably about 104° F. to about 108° F., the aforesaid electrical energy supplying device is connected to said heat source and provides a first temperature rise from said first temperature to a second temperature of about 123° F. to about 127° F., and preferably about 124° F. to about 126° F., during a first period of about 10 to 15 minutes, and thereafter in a second period of about three and one-half minutes increases the temperature of said heat source by providing a third temperature of about 122° F. to about 128° F., preferably about 124° F. to about 126° F., said second and third temperatures differing one from the other and said third temperature being lower than said second temperature, increasing to a temperature differing from said third temperature and being in the range of about 124° F. to about 126° F., and cycling between said second and third temperatures repetitively nine to ten times, preferably seven to eight times, wherein each repetition involving said second and third temperature takes place during a period of about five minutes.

BRIEF DESCRIPTION OF THE DRAWINGS

FIG. 4 is a cross-section of the electrical protection wire.

FIG. 7 illustrates two examples of eating plans that are preferably prescribed in accordance with the invention.

DETAILED DESCRIPTION OF THE INVENTION

At the first session with the subject whose body evidences cellulite, localized or generalized fat, the subject's height and weight measurements are taken, as well as measurements of the subject's waist, hips, right thigh and right knee. Such measurements, for best results, are taken at the beginning of the first session and again every subsequent six sessions. The subject's weight is recorded in the subject's chart at each session and will show the effects as to the extent to which the subject has or has not followed the prescribed eating plan outlined below.

Also at the first session, a Body Composition Test is performed by use of a BIA 450 Bioimpedance analyzer on the wrist and ankle of the subject. Resistance and reactance, the two components of impedance, are measured directly from the body. Using regression analysis, the analyzer assesses the lean body weight, fat mass (or fat body weight), body mass index (BMI), basal metabolic rate (BMR), total body water (TBW), and the ratios: TBW/body weight and TBW/fat-free mass.

In reporting the results of the Body Composition Test, recommendations are made as to the following suggested targets: body fat percentage, total weight, fat weight, lean weight, weight to lose, body water percentage and basal metabolic rate. The Body Composition Test is preferably repeated at the end of the program.

A heat source that can be placed on the subject (including, for example, a patch, cuff, bandage or preferably wrap and most preferably the thermal wrap) is used to apply heat to the affected areas (that is, those areas on the subject's body which exhibit the presence of cellulite, localized or generalized fat). While the wraps may be purchased commercially (at least two different types of wraps are commercially available: localized body wraps and generalized body wraps) and typically comprise a polyurethane layer, wraps specifically designed for use in accordance with the invention and providing a significant measure of safety are described below with reference to FIG. 2A to FIG. 6.

Figure 1:
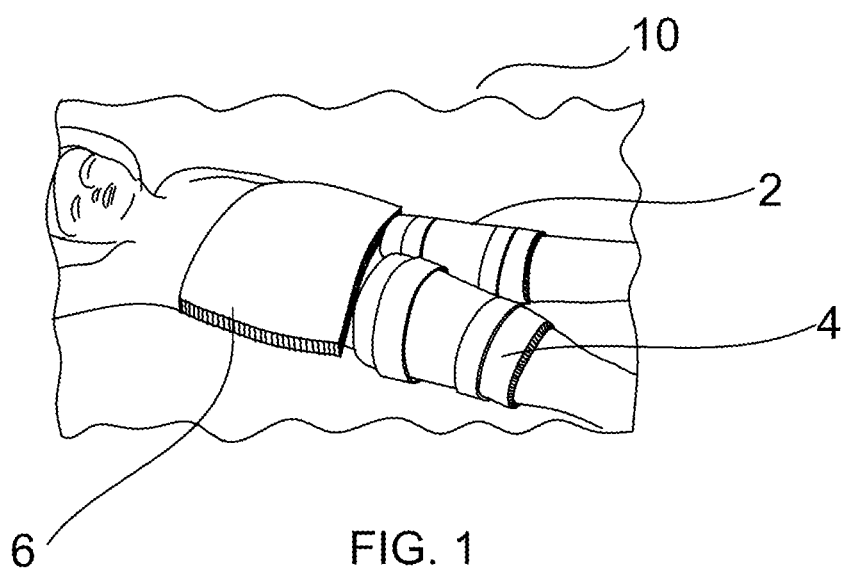
FIG. 1 shows an exemplar series of wraps 10, wherein a left wrap, a right wrap and a top wrap are employed as three individual wraps.

Referring to FIG. 1, a subject is placed in a series of body wraps (10). The exemplar body wraps have three localized body wraps as shown. A left wrap (2) is employed to cover at least the upper portion of the left leg of the subject, whereas a right wrap (4) is employed to cover at least the upper portion of the right leg of the subject and a top wrap (6) is employed to cover a substantial portion of the upper body of the subject. The three independent wraps can be used independently (not shown) or jointly (as shown in FIG. 1). The three wraps have their own respective temperature controls, allowing the user to customize the temperature or heating profiles. The wraps also have safety features detailed in FIGS. 2A to 6. Preferably, the localized wraps are not placed around the subject so as to have overlapping regions, as it gives more comfort to the subject during the procedure. Further, the left and right wraps around the legs can either cover the entire the leg or only a (upper) portion of the legs. Preferably, the left and right wraps cover a significant portion of the upper portion of the legs, where most of the fat is likely to accumulate. More preferably, the left and right wraps leave the areas of the knees uncovered, so that the subject can bend or the move the knees if desired while being wrapped. Localized wraps 2, 4 and 6 are exemplar localized body wraps, which are used for individuals exhibiting cellulite or local fat and are placed around parts of the body, such as thighs (wrap 2 and 4), or hips and the abdomen (wrap 6).

The sizes or dimensions of the localized wraps in FIG. 1 are only for illustration purpose. The localized body wraps are available in various sizes, for example for thighs, wraps between 32 inches to 42 inches by 12 inches to 20 inches are available, and for abdomens, wraps between 46 inches to 60 inches by 18 inches to 28 inches are available.

Typically, a localized body wrap measuring between 32 inches to 42 inches by 12 to 20 inches is placed on the thigh and a wrap measuring between 46 inches to 60 inches by 18 inches to 28 inches is placed on the abdomen and hips.

Optionally, generalized body wraps for use with subjects whose body shows generalized fat can be used for a large size individual and for individuals of average weights, and are placed substantially around the entire body in three sections, including top, the middle and the lower part of the body. The top section typically extends from the shoulders to the abdomen, the middle section extends from the abdomen to below the knees; and the lower section extends from below the knees to the toes. Each of three sections of a generalized body wrap typically measures 22 inches by 56 inches.

In accordance with the invention, both localized body wraps and generalized body wraps are connected to an electrical current source (not shown) using a device configured to regulate an electrical current sufficient to produce the temperature of the wraps, as described below. The device preferably includes a selector for selectively configuring the device to supply current to either a first heat source comprising a localized body wrap or a second heat source comprising a generalized body wrap. Preferably, the localized wraps have independent variable temperature controls, which allow the user to regulate the temperatures independent of other wraps.

The wrap contains electrical circuits with low voltage (24 volts) throughout. They may be secured to the subject's body by Velcro connections. An example of a commercially manufactured wrap is set forth in United States Patent Application Publication No. US 2004/0073258 published on Apr. 15, 2004, the disclosure of which is incorporated by reference herein in its entirety.

Figure 2A:
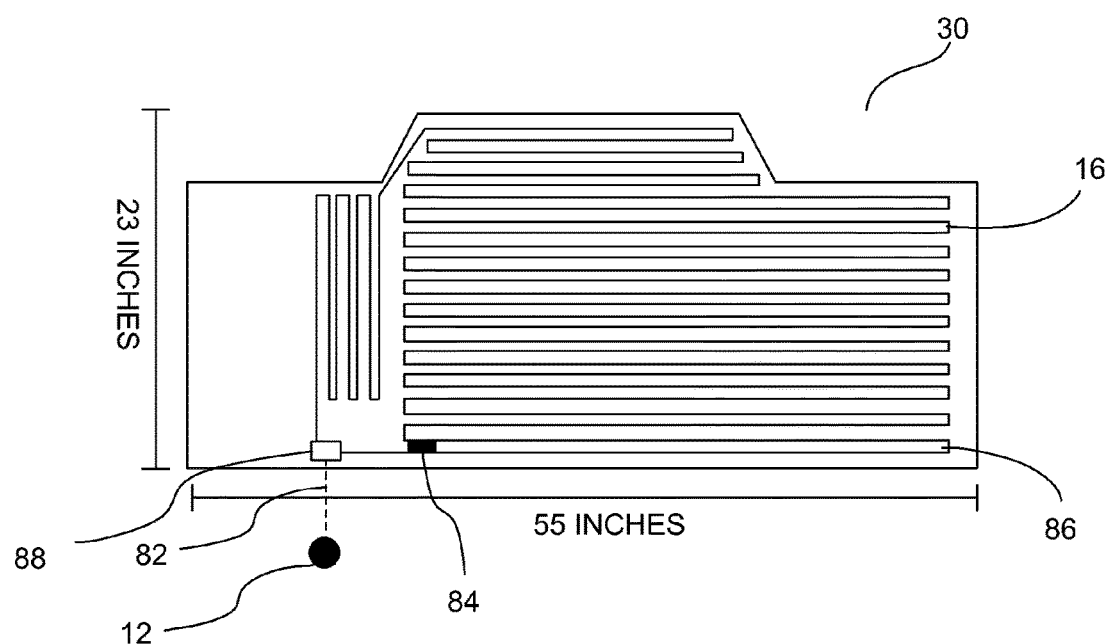
FIG. 2A is a plan view showing interior features of an exemplar body wrap in accordance with the invention.

Referring to FIG. 2A, a body wrap 30, in accordance with the invention, may be of generally rectangular shape having a length L of approximately 59 inches and a width W of approximately 20 inches. A thermostat (not shown), having a set temperature at a maximum of 85° C. provides maximum temperature protection. The provided sensor and thermostat provide for the required temperature control. The regulation of the temperature of wrap 30 is as more fully described below.

Figure 2B:
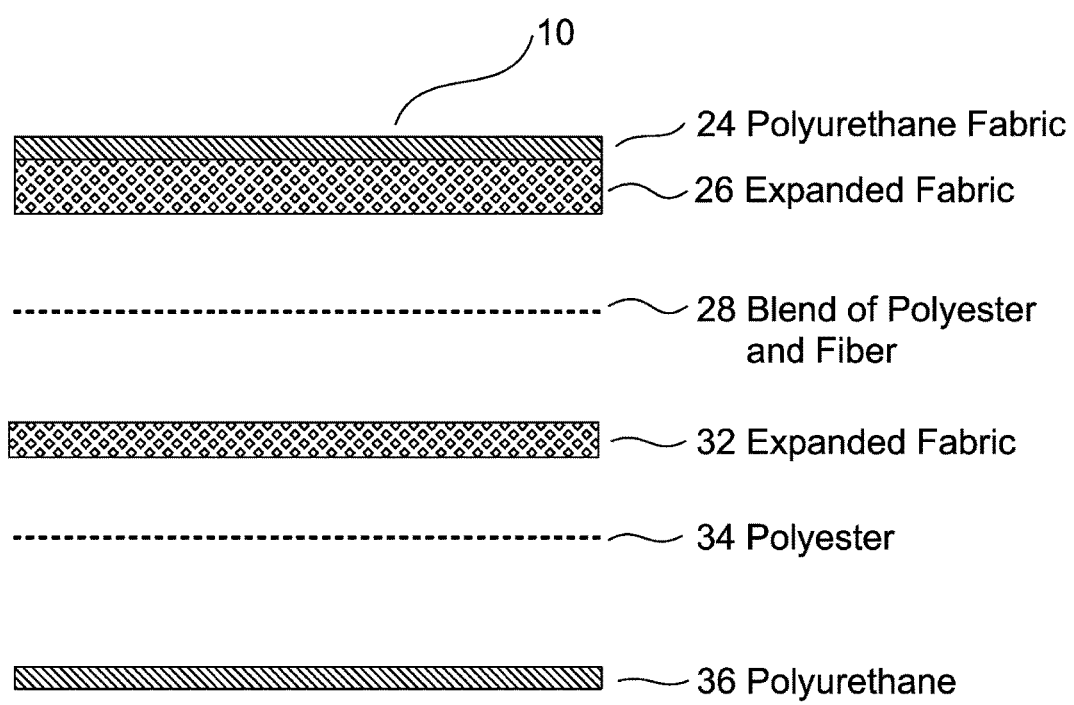
FIG. 2B is a cross-section of the body wrap of FIG. 2A.

Referring to FIG. 2B, the layers of wrap 10 are shown in cross-section, a top layer 24 may be formed of polyurethane fabric. An expanded fabric 26, as for example formed of polyester, may be bonded to layer 24. A layer 28 made of a blend of polyester yarn and fibers is disposed below layer 26. An additional expanded fabric layer 32, formed of polyester, is sandwiched between layer 28 and a further woven or non-woven layer 34. Layers 28, 32, and 34 form a quilted insert between the combination of layers 24 and 26 on one side, and a bottom layer 36 on the other side, formed of a polyurethane fabric. The various layers described above are bonded together, especially at the periphery of the wrap 10, by any of several well known techniques, such as by the use of adhesives, which may be activated under heating under pressure and by sewing the previously arranged plies.

Figure 3:
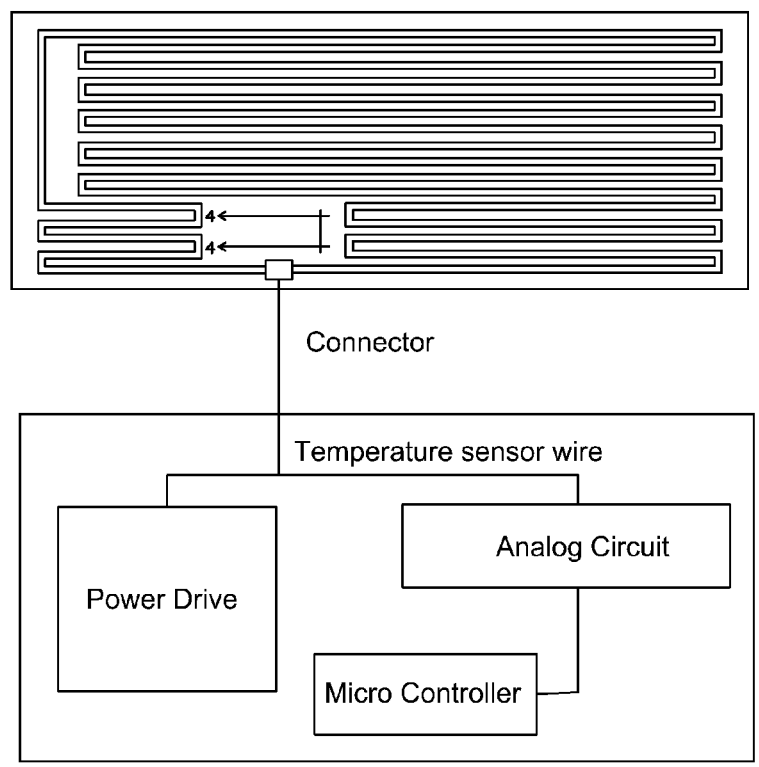
FIG. 3 is an illustration of how the control panel and wraps are connected.

Cable 82 in FIG. 2A can further connect to a control panel as shown in FIG. 3. The control panel includes at least a temperature sensor wire connected to power an analog circuit. The analog circuit is further connected to a micro controller. The temperature sensor wire is one of the exemplar safety features of the present invention.

The temperature sensor wire for receiving and making electrical connections is shown in FIG. 3.

In one embodiment of the present invention (see FIG. 4), the temperature sensitive wire includes at least the following: a resistive heating wire wound around an insulating polyester core of coaxially arranged wire. A coaxial insulator separates resistive heating wire from an electrical protection wire wound around the insulator. An outer insulator surrounds the wire and forms the outer covering of the cable. All of these components of the temperature sensitive wire are flexible to allow for easy routing of the wire through the wrap in any required arbitrary path. Insulators may be formed so as to be heat shrinkable, with heat being applied after winding of the wire on the core and the wire on the insulator, respectively.

The foregoing arrangement helps to further assure safety. The wire may be connected to a system ground in controller 50 (not shown). If there is a break in the heating wire and insulator, any risk of shock is avoided, because generally, there will be contact of the heating wire with the protection wire, thus establishing a short circuit. This contact is detected as a sudden change in resistance measured by power circuit (not shown), which may be configured to shut down power.

Figure 5:
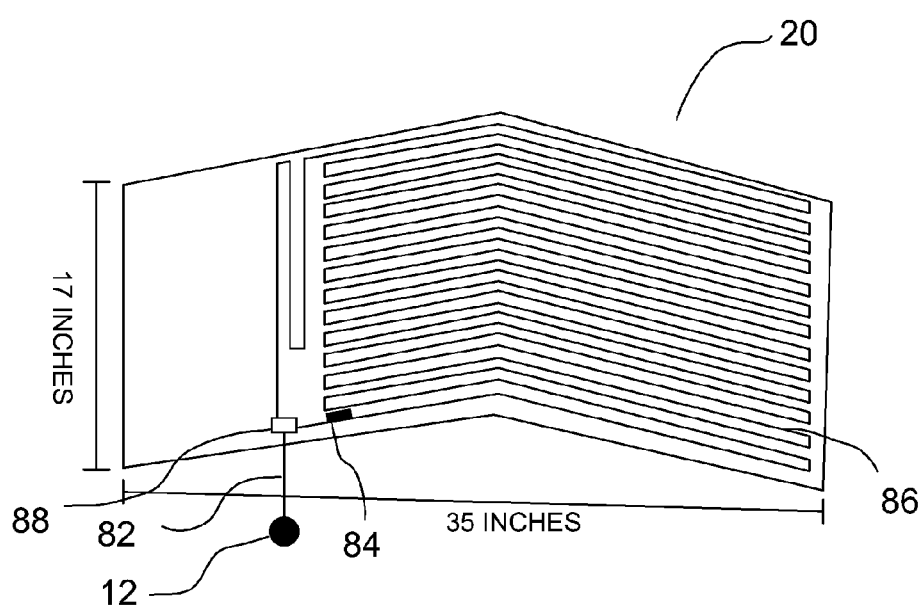
FIG. 5 is a plan view showing interior features of the exemplar body wrap in accordance with the invention.

FIG. 5 illustrates a cross section view of another alternative embodiment of the safety features of the present invention. The safety features as shown include at least a temperature sensor layer and an insulation layer which are sandwiched in between two external insulation layers.

FIG. 2A and FIG. 5 illustrate, respectively, a wrap 20 suitable for use around the thigh (FIG. 2A) and a wrap 30 suitable for use around the lower and middle torso (abdominal section) of the body (FIG. 5). Wrap 30 comprises an electrical connection 88, electrical resistance 86, supply wire 82, thermostat 84 and connector 12.

Although the general shapes and dimensions of wraps 20 and 30 in FIGS. 2A and 5 are different, the construction and principles of operation are essentially the same as described with respect to the embodiment of FIG. 2A to FIG. 5. Wrap 20 has a V shape, but may have a dimension of L of approximately 32.7 inches and dimension L' of approximately 16.5 inches. It may consume about 90 watts. Wrap 30 may have major dimensions of length L" equal to 54.3 inches and an extended width W" of 22.8 inches, and may also operate at a power of approximately 90 watts. A portion of wrap 30 may extend over the midriff section of a user, or slightly above (FIG. 2A).

The wraps, and in particular the wraps in accordance with the invention, are preheated during a "warm-up" phase to approximately 104° F. to 108° F., and preferably 106° F. to 108 F. After the wraps are pre-heated to the 104° to 108° F. range, the wraps are placed on the subject. Between the wraps and the subject's skin, there is placed a sheet of plastic, preferably made of low-density polyethylene, for hygienic purposes to prevent perspiration from the subject's body from coming into contact with the wraps. The thermal wrap temperature in accordance with the invention increased to a temperature associated with a fever and namely 98.6° F.

After placement of the pre-heated wraps on the subject, the treatment begins with the startup cycle for approximately the next twelve to fifteen minutes, but preferably ten to fifteen minutes, wherein the temperature of the wraps is increased to a temperature with the range of 122° F. to 134° F., and preferably within a range of 124° F. to 126° F.

At the end of the startup cycle, the first five-minute treatment cycle will commence. For approximately the next three and one half minutes, the temperature of the wraps is increased again to a value within the range of approximately 122° F. to 134° F., and preferably a temperature within the range of 124° F. to 126° F.

The treatment cycle by variable temperature that characterizes the invention has two phases:

(1) turning off the current in the wraps until the temperature of the wraps decreases to a temperature value of between 112° F. to 120° F., but generally only as low as 110° F. to 114° F. over the following approximately two-minute period, as influenced by the maximum temperature and by environmental considerations, the temperature being different and having a lower value than the value in step (2); and (2) increasing the temperature over an approximate three minute period to a value between 122° F. and 134° F.;

and is repeated until the ninth or tenth repetition of such treatment cycle.

At the end of the ninth or tenth repetition of such treatment cycle, approximately between 50 and 55 minutes will have elapsed from the time that the wraps were initially placed on the subject's body. At room temperature, the average temperature of the skin is typically at approximately 98° F. During the treatment cycle, the average skin temperature is approximately 110° F.

Figure 6:
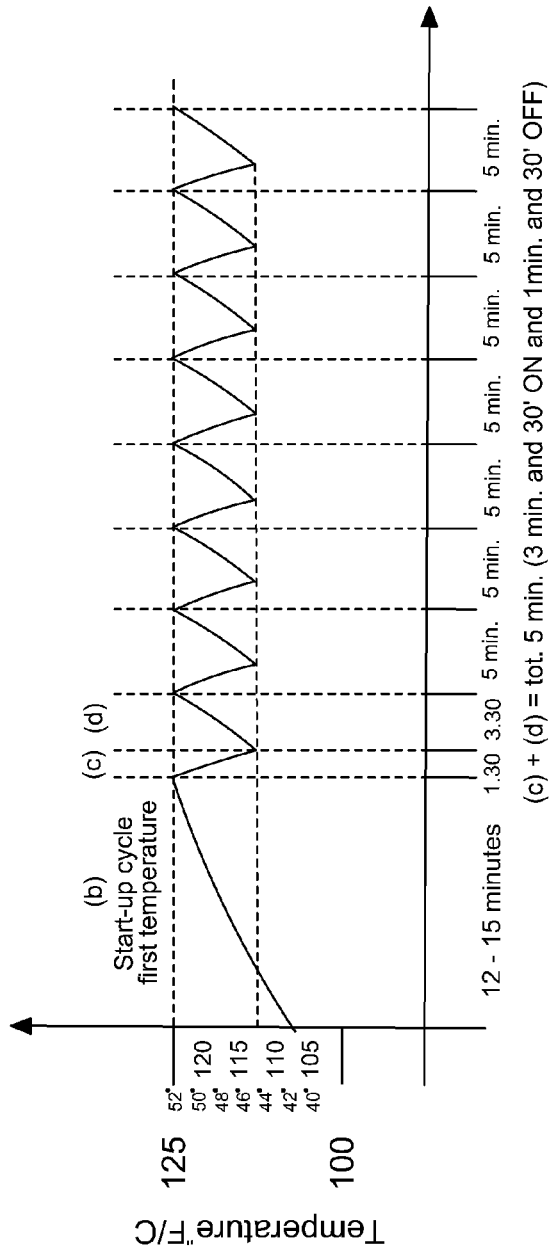
FIG. 6 is a chart that graphically depicts the variable temperature of the wraps during the heat treatment process, the normal skin temperature, and the average skin temperature during the treatment process.
Figure 8:
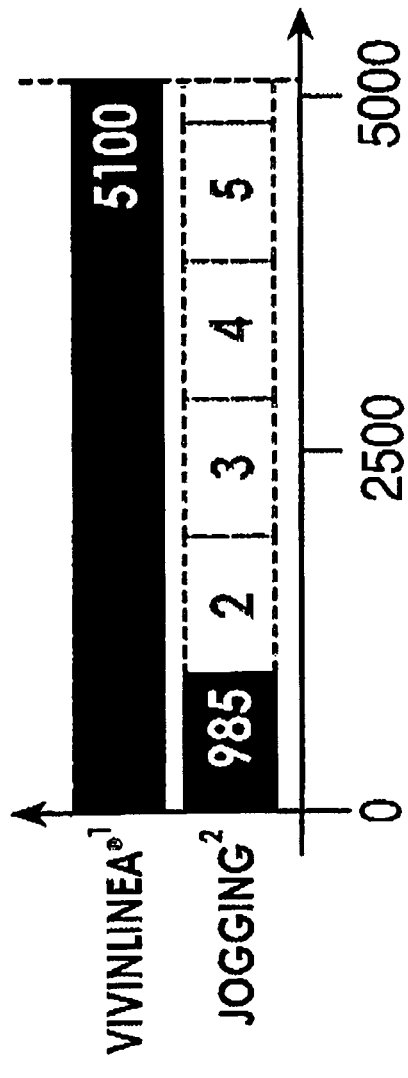
FIG. 8 illustrates a comparison between calories burnt by the thermal therapy of the present invention and jogging.

The steps outlined above are shown in FIG. 6.

At the end of the ninth or tenth repetition of the treatment cycle, the wraps and the plastic are removed from the subject's body and the subject remains in a prostrate position for the next three to five minutes to reestablish his or her blood pressure, which typically is lowered during the treatment.

The heat source temperature cycles and specifically the conductive heating system by variable temperature of the invention produce the results as set forth in the following:

The application of the heat treatment outlined above increases the subject's circulation and induces the flow of blood to the surface of the skin. Blood that is transported to the surface of the skin is richer in oxygen and nutrients and gives the skin the appearance of normality, as opposed to the orange tinge that appears as a result of the presence of cellulite. Also, the presence of additional oxygen in the blood activates a pumping mechanism (the ATP pump) located on the membrane of the fat cell. Fat that is deposited into the cell is expelled from the cell, as a result of the pumping action of the ATP pump, into the lymphatic system and eventually to the liver.

Preferably, following the subject's five to ten minute resting period, the subject takes a shower in three phases: (1) the first phase, lasting approximately 1.5 minutes, with the water temperature at approximately 95° F.; (2) the second phase, lasting approximately 40 seconds, with the water temperature at approximately 75° F.; and (3) the third phase, lasting for approximately 30 seconds, with the shower just on the legs at a cold water temperature, preferably between 41° F. and 59° F.

The shower has multiple beneficial effects, including the slowing or stopping of perspiration by the subject, a toning of the body, reinforcement of the immune system, aid in circulation of the subject's blood and overall enhancement of the process of reducing cellulite.

Preferably, no more than one to three days should elapse between the end of this treatment and the next session with the subject, at which time, the steps outlined above are repeated. The treatments are continued, preferably with 24 hours to 72 hours between every two sessions, until such time as the subject has reached his or her targets set forth in the recommendations resulting from the Body Composition Test.

The treatment may also involve, before or following the removal of the wraps, but in any event before the shower, additional treatments such as manual or vibratory massage, lymphatic drainage, seaweed mud, fango- or thalassotherapy, ionophoresis, ultrasound, electrostimulation or hot spring water baths.

Preferably, the treatment outlined above is performed in conjunction with an appropriate eating plan. Such plan provides for the daily intake of between 1,300 and 2,000 calories, and the consumption of a minimum of 25 to 30 grams of fiber.

In this plan, the main courses, lunch and dinner, commence with two to three servings of raw mixed salad, rich in radishes (preferably organic), and dressed with one tablespoon of extra virgin olive oil and lemon.

The plan also provides that certain categories of food are preferably consumed together, in regulated portions, at any one meal. Thus, complex carbohydrates or starches (for example, bread, pasta, potatoes and other foods falling within this category) are preferably not consumed in a proportion greater than 20% by weight of either animal protein (for example, fish, poultry, meat, eggs and other foods falling within this category) or vegetable protein (for example, beans, chickpeas, lentils and other foods falling within this category) that is consumed during the same meal.

Thus, if 10 ounces of animal protein or vegetable protein are consumed during a meal, it is preferable that no more than two ounces of complex carbohydrates (and even more preferably no more than one ounce of the latter) be consumed during the same meal. Conversely, if 10 ounces of complex carbohydrates are consumed, then no more than two ounces of animal protein or vegetable protein (and more preferably no more than one ounce) should be consumed during the same meal. At least three quarters of a cup of steamed, cooked or baked vegetables is preferably consumed at any meal where animal protein or complex carbohydrates, or both, are consumed.

Optimally, the majority of the food consumed at breakfast or lunch is composed of complex carbohydrates or vegetable protein. Preferably, protein consumption at dinner should alternate, for example, vegetable protein should be consumed on Monday, Wednesday and Friday, and animal protein consumed on Tuesday, Thursday, Saturday and Sunday.

Foods within the fruit group are preferably consumed as snacks, without food from other groups, and are not consumed with vegetables or animal protein or complex carbohydrates.

As an example of eating plans, Plan One, set forth in FIG. 7, is preferably followed during the work week. Plan One includes a hearty breakfast, a light lunch, dinner and two or three snacks according to the following regimen: Snack (60 to 80 calories in the fruit group); Breakfast (165 to 440 calories); Light Lunch (340 to 440 calories); Snack (80 calories in the fruit group); Dinner (780 to 1,470 calories); and Snack (10 to 80 calories in the fruit group). As noted, it is preferable that the daily caloric intake be a minimum of 1,300 calories and a maximum of 2,000 calories.

Plan Two, as set forth in FIG. 7, is preferably followed during weekends and includes a light breakfast, lunch, dinner and three snacks according to the following regimen: Snack (60 to 80 calories in the fruit group); Light Breakfast (10 to 80 calories); Snack (80 calories in the fruit group); Lunch (690 to 1,040 calories); Dinner (725 to 1,470 calories); and Snack (10 to 80 calories in the fruit group). As with Plan One, it is preferable that the daily caloric intake be a minimum of 1,300 and a maximum of 2,000.

Plans One and Two are complemented with a selection by the subject of a "Cleansing Day" where the subject chooses one day a week to detoxify his or her body by having five or six fresh fruit snacks, two servings each, every two hours through the day and two (2) three-serving salads, one at lunch with one-third cup of almonds (6-8) and another at dinner with one-half medium avocado.

Preferably, the eating plan includes a prescription that at least 16 ounces of natural filtered water be consumed daily between main courses, preferably on an empty stomach.

The inventors are aware that adherence to the method and treatment outlined above can result in the burning of up to 2,500 calories from localized fat deposits at any given session of treatment.

The combination of the heat treatment outlined above and adherence to the eating plan produces a synergistic effect in reducing cellulite, local or generalized fat in a healthy, non-invasive manner in total relaxation.

It has been found to be important to have adequate skin care during a weight reduction program. A skin care product line such as that produced by Gruppo Biofarma Via Castelliere, of Italy, and imported into the United States by VIVNLINEA CORP. of Great Neck, N.Y., may be used. These products, suitable for home-use, have been developed for specific areas of the body, such as: waist, hips, abdomen, bust, shoulders, arms, legs, thighs and knees. They complement the treatment provided as disclosed herein. The principal benefits include hydrating, nourishing, softening and firming skin, as well as slowing or halting aging of the skin. The principal natural ingredients of these creams include sweet almond oil, wheat germ oil, focus, vesiculosus, kelpadelie, rhodysterol, codium tomentosum, alga rosa, corallinea officinalis, kaolin and horse chestnut, as well as extracts of: hops, horsetail, fenu-Greek, green coffee, guaraná, green tea and butcher broom. Also included may be a mix of essential oils such as origanum, rosemary, lemon, bergamot and ylang.

The skin care products may be used during or after a session, and may be used at home for long-term maintenance.

Although the present invention has been described in considerable detail with reference to certain preferred embodiments thereof, the invention may be embodied in other forms or carried out in other ways without departing from the spirit and scope of the invention. Therefore, the claims that follow should not be limited to the preferred embodiments described herein.

The invention claimed is:

1. A method for reducing cellulite, local or generalized fat in a person having such condition, comprising the steps of:
   (a) applying a heat source, having a temperature within the temperature range of about 104° F. to about 108° F. (first temperature), to the area on the body of a person affected with cellulite or local fat;
   (b) increasing the temperature of said heat source over approximately the next twelve to fifteen minutes to a second temperature different from the temperature in step (a) in the range of about 122° F. to about 134° F.;
   (c) decreasing the temperature of said heat source over approximately the next one and one-half minutes to ten minutes to a third temperature differing from said second temperature and being in the range of about 112° F. to about 120° F.;
   (d) increasing the temperature of said heat source over approximately the next three and one-half minutes to a temperature differing from said third temperature by having a higher value than said third temperature and being in the range of about 122° F. to about 128° F.; and
   (e) repeating a cycle of the steps (c) and (d) nine or ten times until a period of about 45 minutes to about 55 minutes has elapsed from the time that said heat source was applied to said affected area.

2. The method of claim 1 wherein said heat source comprises a polyurethane wrap member.

3. The method of claim 1 wherein said heat source comprises a low voltage heating element.

4. The method of claim 1 comprising the further steps of determining the lean body weight and size of the waist, hips, thighs and knees of said person.

5. The method of claim 1 comprising the further step of determining the body fat percentage of said person.

6. The method of claim 1 comprising the further step of determining the basal metabolic rate of said person.

7. The method of claim 1 comprising the further step of determining the total body water of said person.

8. The method of claim 1 comprising the further step of determining the ratio of the total body weight to the fat-free mass of said person.

9. The method of claim 1 comprising the further step of prescribing an eating plan with a daily caloric intake of about 1,300 to about 2,000 calories.

10. The method of claim 9 comprising the further step of prescribing a meal where food containing complex carbohydrates is consumed by said person in a proportion not greater than 20% by weight to food containing animal protein that is consumed during said meal by said person.

11. A method for reducing cellulite, local or generalized fat in a person having such condition, comprising the steps of:
   (a) applying a heat source, having a temperature within the temperature range of about 104° F. to about 114° F. (first temperature), to the area on the body of a person affected with cellulite or local fat;
   (b) increasing the temperature of said heat source over approximately the next ten to fifteen minutes to a second temperature different from the temperature in step (a) in the range of about 123° F. to about 127° F.;
   (c) decreasing the temperature of said heat source over approximately the next one and one-half minutes to ten minutes to a third temperature differing from said second temperature and being lower than said second temperature and being in the range of about 113° F. to about 119° F.;
   (d) increasing the temperature of said heat source over approximately the next three and one-half minutes to a temperature differing from said third temperature by having a higher value than said third temperature and being in the range of about 123° F. to about 127° F.; and
   (e) repeating a cycle of the steps (c) and (d) nine or ten times until a period of about 50 minutes to about 55 minutes has elapsed from the time that said heat source was applied to said affected area.

* * * * *